(12) United States Patent
Urleb et al.

(10) Patent No.: US 7,285,547 B2
(45) Date of Patent: Oct. 23, 2007

(54) AMIDINOPHENYLALANINE DERIVATIVES AS THROMBIN INHIBITORS

(75) Inventors: Uros Urleb, Ljubljana (SI); Anamarija Zega, Ljubljana (SI); Mojca Stegnar, Ljubljana (SI); Bakija Alenka Trampus, Ljubljana (SI); Tomaz Solmajer, Ljubljana (SI); Gregor Mlinsek, Skofja Loka (SI)

(73) Assignee: LEK Pharmaceuticals d.d., Ljubjana (SI)

( * ) Notice: Subject to any disclaimer, the term of this patent is extended or adjusted under 35 U.S.C. 154(b) by 470 days.

(21) Appl. No.: 10/433,358

(22) PCT Filed: Dec. 20, 2001

(86) PCT No.: PCT/IB01/02600

§ 371 (c)(1),
(2), (4) Date: Jun. 3, 2003

(87) PCT Pub. No.: WO02/051824

PCT Pub. Date: Jul. 4, 2002

(65) Prior Publication Data

US 2004/0048851 A1 Mar. 11, 2004

(30) Foreign Application Priority Data

Dec. 22, 2000 (SI) ............................... 200000326

(51) Int. Cl.
*A61P 7/02* (2006.01)
*A61K 31/55* (2006.01)
*C07D 295/20* (2006.01)

(52) U.S. Cl. ............................ 514/217.07; 514/217.11; 540/597; 540/607

(58) Field of Classification Search ........... 514/217.07, 514/217.11; 540/597, 607
See application file for complete search history.

(56) References Cited

FOREIGN PATENT DOCUMENTS

WO    WO95/13274    5/1995

OTHER PUBLICATIONS

Zega, et al., 2001, "Design and Structure-Activity Relationship of Thrombin Inhibitors with an Azaphenylalanine Scaffold: Potency and Selectivity Enhancements Via P2 Optimization," *Bioorg. Med. Chem.*, vol. 9, pp. 2745-2756, Pergamon Press.

Oh, et al., 1998, "Discovery of LB30057, A Benzamidrazone-based Selective Oral Thrombin Inhibitor," *Bioorg. Med. Chem. Lett.*, vol. 8, pp. 631-634, Pergamon Press.

Kim, et al., 1997, "Rational Design of Selective Thrombin Inhibitors," Bioorg. Med. Chem. Lett., vol. 7, No. 7, pp. 769-774, Pergamon Press.

*Primary Examiner*—Brenda Coleman
(74) *Attorney, Agent, or Firm*—Bromberg & Sunstein LLP

(57) ABSTRACT

The compounds of the formula (formula 1) and pharmaceutically acceptable salts thereof and a process for preparing the same and pharmaceutical compositions containing the same are described wherein the substituents have the meaning as specified in the description. The compounds are used as thrombon inhibitors.

7 Claims, No Drawings

AMIDINOPHENYLALANINE DERIVATIVES AS THROMBIN INHIBITORS

CROSS REFERENCE TO RELATED APPLICATIONS

This application is a national stage entry under 35 U.S.C. § 371 of PCT/IB01/02600, filed Dec. 20, 2001, which in turn claims priority from Slovenian application number P-200000326, filed Dec. 22, 2000.

TECHNICAL FIELD

The invention belongs to the field of pharmaceutical industry and relates to novel azaphenylalanine derivatives, procedures for their preparation and pharmaceutical compositions containing them. Novel azaphenylalanine derivatives have the enzymatic activity (serine proteases) and anticoagulant effect.

TECHNICAL PROBLEM

There exists a constant need for new medicinal products with anticoagulant activity that may be administered either orally or parenterally and that are highly selective and of low toxicity. Recently, low molecular weight thrombin inhibitors appear to be of growing importance in this area.

PRIOR ART

Thrombin as a serine protease is one of key enzymes in the processes of blood coagulation and in the development of thrombosis (Edit, J. F.; Allison, P.; Noble, S.; Ashton, J.; Golino, P.; McNard, J.; Buja, L. M.; Willerson, J. T., *J. Clin. Invest.* 1989, 84, 18.).

The crystalline structure of serine proteases of thrombin and serine is known (Bode, W.; Turk, D.; Karshikov, A. J., *Protein Sci.* 1992, 1, 426).

Currently used anticoagulant agents are toxic and of limited effectiveness.

Low molecular weight thrombin inhibitors should have selective efficacy and can be used in oral administration. There are reversible and irreversible thrombin antagonists (Kimball, S. D., *Curr. Pharm. Design* 1995, 1, 441, Das, J.; Kimball, S. D., *Bioorg. Med. Chem.* 1995, 3, 999, Kimball, S. D., *Blood Coagulation and Fibrinolysis* 1995, 6, 511, Breznik, M.; Peèar, S., *Farm. Vestn.* 1997, 48, 545, Sanderson, P. E. J.; Naylor-Olsen, A. M.; *Current Med. Chem.* 1998, 5, 289, Rewinkel, J. B. M.; Adang, A. E. P., *Curr. Pharm. Design* 1999,5,1043, Wiley, M. R.; Fisher, M. J.; Exp. Opin. Ther. Patents 1997, 7, 1265, Menear, K.; *Current Med. Chem.* 1998, 5, 457.

The majority of reversible thrombin antagonists derive from peptidomimetically modified structure D-Phe-Pro-Arg. The aim of the modification is to provide chemical stability, selectivity and effectiveness.

The active substance used in Japan and the USA is argatroban (Kikumoto, R.; Tamao, Y.; Tezuka, T.; Tonomura, S.; Hara, H.; Ninomiya, K.; Hijikata, A.; Okamoto, S., *Biochemistry* 1984, 23, 85).

Amidinophenylalanine derivatives and aminopyridylalanine derivatives have selective antithrombotic activity (Danilewicz, J., et al. WO 95/13274 (1995)).

By replacing amidino-pyperidine P1 group with a weakly basic 2-amino-6-metylpyridine structure, a selective and effective thrombin inhibitor that can be used in oral administration has been obtained (Sanderson, P. E. J.; et al., *Bioorg. Med. Chem.* 1998, 8, 817).

SI 20025 describes thrombin inhibitors which are the derivatives of azaphenylalanine.

Accordingly, the object of the present invention is to overcome the problems encountered in the prior art.

DESCRIPTION OF THE SOLUTION OF TECHNICAL PROBLEM INCLUDING EXAMPLES

The above problems are solved e.g. by a compound as defined in claim 1 and a process as defined in claim 6 as well as pharmaceutical compositions as defined in claim 8.

The invention relates particularly to novel azaphenylalanine derivatives and analogs thereof of the general formula (I)

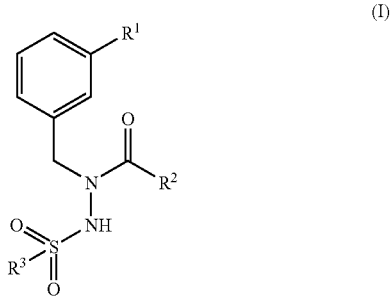

wherein
$R^1$ represents a residue of the formula

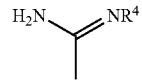

wherein $R^4$=H, alkyl ($C_1$-$C_3$), OH, O-alkyl ($C_1$-$C_3$), $NH_2$;
$R^2$ represents a residue of the formula

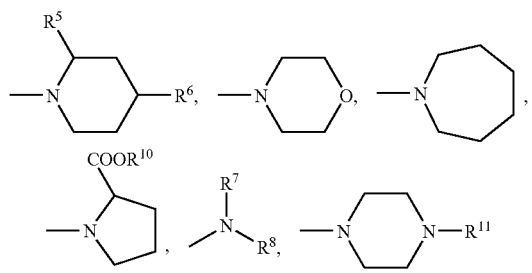

wherein $R^5$H, alkyl (C1-C3), $CF_3$, $COOR^9$,
$R^6$=H, alkyl ($C_1$-$C_3$), $CF_3$, $COOR^9$,
$R^7$=alkyl (C1-C3), cycloalkyl (C3-C0),
$R^8$=alkyl ($C_1$-$C_3$), cycloalkyl (C3-C6),
$R^9$=H, alkyl ($C_1$-$C_3$),
$R^{10}$=H, alkyl ($C_1$-$C_3$), benzyl
$R^{11}$=H, $SO_2Me$, $CO_2Me$;

$R^3$ represents a residue of the formula

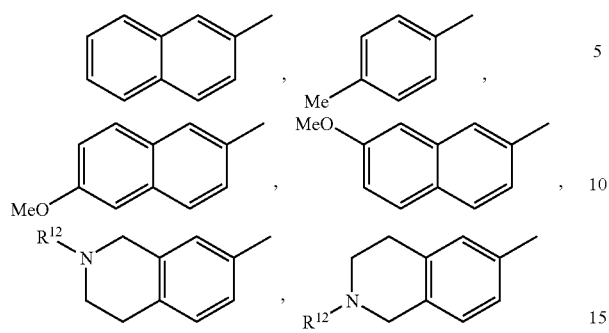

wherein $R^{12}$=H, alkyl ($C_1$-$C_3$), acetyl
and pharmaceutically acceptable salts thereof.

In comparison to the compounds, described in SI 20025, the compounds of the present invention are of greater activity. Ki thrombin (μM) of the compound a, according to the patent SI 20025, is 0.032, Ki thrombin (μM) of the compound b, according to the present invention, is 0.005.

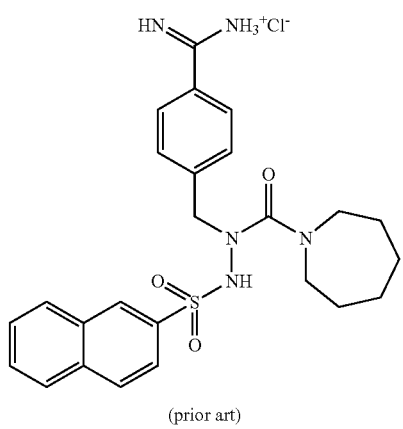

a (prior art)

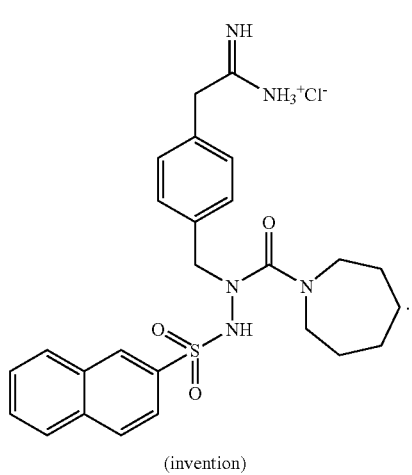

b (invention)

The invention also particularly relates to a process for the preparation of azaphenylalanine derivatives and analogs of the general formula (I).

They may be suitably prepared as follows:

a) 3-cyanobenzaldehyde of formula (II)

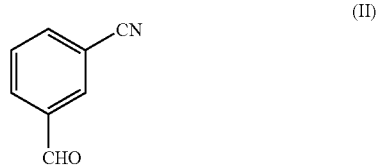

is converted with BOC-carbazate of the formula (III)

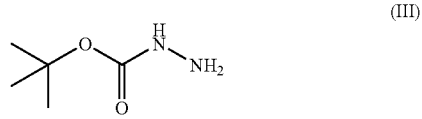

to the compound of the formula (IV),

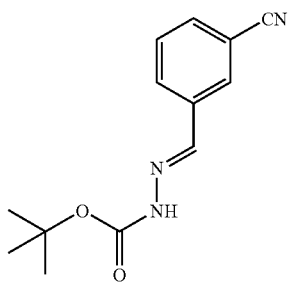

which is subjected to reduction by catalytic hydrogenation or with NaCNBH$_3$ and is converted to the compound (V),

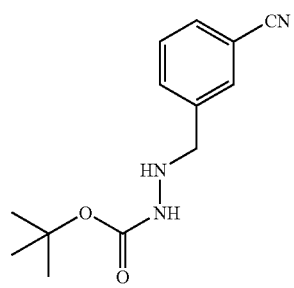

which reacts with triphosgene and amine of the formula (VI),

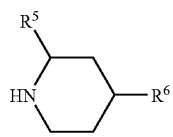

wherein $R^5$ and $R^6$ have the same meanings as in the formula (I),
or with triphosgene and amine of the formula (VII or VIII),

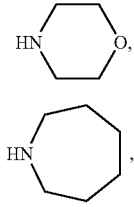

(VII)

(VIII)

or with triphosgene and amine of the formula (IX),

(IX)

wherein $R^7$ and $R^8$ have the same meanings as in the formula (I),
or with triphosgene and amine of the formula (X),

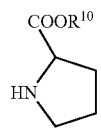

(X)

wherein $R^{10}$ has the same meaning as in the formula (I), in "one pot" reaction to the compound (XI)

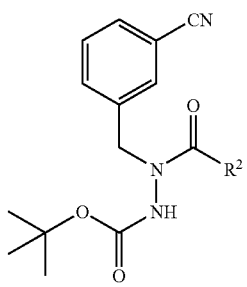

(XI)

wherein $R^2$ has the same meaning as in the formula (I).
The protecting BOC group in the compound (XI) is removed with HCl (g) in HOAc at room temperature to obtain the compound (XII),

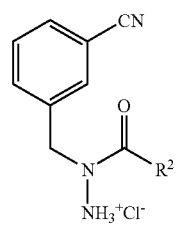

(XII)

wherein $R^2$ has the same meanings as in the formula (I) which reacts with aromatic sulfonylchloride up to the compound (XIII),

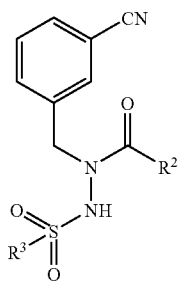

(XIII)

wherein $R^2$ and $R^3$ have the same meanings as in the formula (I).

The compound (XIII) is converted to the compound of the formula (I)

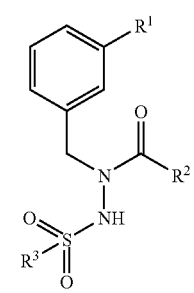

(I)

in a usual manner. This can be achieved e.g. by converting compound (XIII) by addition of a hydroxylamine and an anhydrous alcohol such as e.g.—ethanol or a mineral acid such as e.g. HCl(g) and e.g. ammonium acetate, thus obtaining compound (I).

When the compound (XIII) reacts with hydroxylamine in anhydrous ethanol, $R^4$ denotes OH group, after the reaction of the compound (XIII) with HCl (g) and ammonium acetate $R^4$ denotes hydrogen.

The starting compounds are prepared, unless otherwise directed, according to the procedures described in the literature; e.g., the compound of the formula IV as described by A. Fäissler, et. al., J. Med. Chem. 1996, 39, 3203-3215.

The invention further relates to the use of compounds of the formula I as therapeutically active compounds. The novel compounds are preferably thrombin inhibitors. They inhibit thrombin and formation of fibrin. They are useful in the treatment or prevention of a variety of thrombosis forms: (i) venous thromboembolism due to formation of a thrombus within a vein (venous thrombosis) associated with acquired (prolonged bedrest, surgery, injury, malignancy, pregnancy and postpartum states or inherited (deficiency of natural coagulation inhibitors) risk factors, obstruction or occlusion of a lung artery by a detached thrombus (pulmonary embolism), (ii) cardiogenic thromboembolism due to formation of a thombus in the heart associated with cardiac arrythmia, heart valve defect, prosthetic heart valves or heart disease, embolism of peripheral arteries caused by a detached thrombus, most commonly in the brain (ischemic stroke), (iii) arterial thrombosis due to underlying atherosclerotic processes in the arteries which obstructs or occludes an artery and causes myocardial ischemia (angina pectoris, acute coronary syndrome) or heart muscle death cell (myocardial infarction), obstructs or occludes a peripheral artery (ischemic peripheral artery disease) and obstructs or occludes the artery after the procedure on the blood vessel (reocclusion or restenosis after transluminal coronary angioplasty, reocclusion or restenosis after percutaneous transluminal angioplasty of peripheral arteries) and (iv) in the number of states (e.g., in complications in pregnancy, in metastazing malignant diseases, after extensive injuries, in bacterial sepsis) when thrombogenic activation causes widespread formation of thrombi within the vascular system (disseminated intravascular coagulation).

The compounds of the present invention may be also used as an adjunct therapy in conjunction with thrombolytic therapy in recent myocardial infarction, in combination with aspirin in patients with unstable angina pectoris designed to undergo percutaneous transluminal angioplasty and in the treatment of patients with thrombosis and with heparin-induced thrombocytopenia.

The compounds of the present invention may further be used for the prevention of coagulation of blood which is in contact with nonbiological surfaces (vascular prosthesis, vascular stents, prosthetic heart valves, extracorporeal circulation systems, hemodialysis) and in vitro to prevent coagulation in biological samples for testing or storage.

The present invention also relates particularly to pharmaceutical compositions comprising the compounds of the formula I. They can be formulated as injectable or oral formulations. The active drug component may be combined with suitable standard additives with respect to the intended form of administration. The pharmaceutical compositions may be prepared according to the standard procedures. The preparation may be formulated in such a manner as to permit controlled and sustained release of the active ingredient. Dosage, frequency and mode of administration depend on a variety of factors, they also depend on individual active ingredient and its pharmacokinetic parameters and on the patient's therapeutic needs.

In Vitro Assays for Determining Proteinase Inhibition

Coagulation Assays

The Anticoagulant effect of thrombin inhibitors was measured by thrombin time (TT), activated partial thromboplastin time (aPTT), and prothrombin time (PT) assays. Inhibitors were added to normal pooled human plasma over a range of concentrations and clotting was recorded in an automated coagulometer (Fibrintimer, Dade/Behring). The concentration of inhibitor that doubled the clotting time was determined for each assay.

1. Thrombin Time (TT)

a) Principle of Method

In a plasma sample thrombin converts fibrinogen into fibrin and the clot is formed. The time for clot formation was measured. Thrombin time is prolonged due to disorders in fibrin polymerisation or due to the presence of thrombin inhibitors.

b) Reagents

Thrombin (Test Thrombin Reagent, 1.5 IU/mL, Dade/Behring): lyophilized bovine thrombin was dissolved in 5 mL of HEPES (25 mmol/L, pH 7.4). The reagent was warmed to 37° C. prior to the assay.

Normal pooled plasma: venous blood from 11 apparently healthy volunteers was collected (1 part 0.11 mol/L sodium citrate solution with 9 parts of blood) and centrifuged immediately at 2000×g for 30 minutes at 4° C. Plasma was removed, pooled and stored in aliquots at −70° C. until use.

Inhibitors: were dissolved in DMSO (10 mM stock solution) and diluted with distilled water to working solutions (the highest concentration 100 μM).

c) Method

Inhibitors (10 μL working solution, concentrations from 2.5 μM to 100 μM) and pooled plasma (90 μL) were incubated at 37° C. for 5 minutes and then thrombin (200 μL) was added. Clot formation was measured in a coagulometer in duplicate.

2. Activated Partial Thromboplastin Time (aPTT)

a) Principle of Method

Incubation of plasma with the optimal quantity of phospholipids and a surface activator leads to activation of factors of the intrinsic coagulation pathway. The addition of calcium ions triggers the coagulation process. The time of fibrin clot formation wass measured. aPTT was used as a screening test for coagulation disorders of the intrinsic coagulation pathway. It is prolonged due to intrinsic coagulation factors deficit or due to the presence of inhibitors.

b) Reagents

Pathromtin SL (Dade/Behring): silicon dioxide particles, vegetable phospholipids, sodium chloride (2.4 g/L), Hepes (14.3 g/L, pH 7.6), sodium azide (<1 g/L). The reagent was used at room temperature (15-25° C.).

Calcium chloride solution: 0.025 mol/L, warmed to 37° C.

Normal pooled plasma: venous blood from 11 apparently healthy volunteers was collected (1 part 0.11 mol/L sodium citrate solution with 9 parts of blood) and centrifuged immediately at 2000×g for 30 minutes at 4° C. Plasma was removed, pooled and stored in aliquots at −70° C. until use.

Inhibitors: were dissolved in DMSO (10 mM stock solution) and diluted with distilled water to working solutions (the highest concentration 100 μM).

c) Method

Inhibitor (10 μL working solution, concentrations from 5 μM to 100 μM) and pooled plasma (90 μL) were incubated at 37° C. for 5 minutes. Pathromtin (100 μL) was added and the sample was incubated for another 2 minutes at 37° C. The addition of calcium chloride (100 μL) triggered the coagulation process and clot formation was detected with a coagulometer in duplicate.

3. Prothrombin Time (PT)

a) Principle of Method

An optimal amount of thromboplastin and calcium are added to plasma sample and the time of fibrin clot formation wass measured. PT is a rapid, sensitive screening test for coagulation disorders of the extrinsic pathway. It is well suited for the induction and monitoring of oral anticoagulant therapy, for diagnosing genetic or acquired deficiencies in coagulation factors and checking the synthesis performance of the liver in hepatic diseases. PT is prolonged due to extrinsic coagulation factors deficit or due to the presence of inhibitors.

b) Reagents

Thromboplastin (Thromborel S, Dade/Behring): was dissolved in 4 mL of distilled water. Reagent was at 37° C. prior to use at least 30 minutes.

Normal pooled plasma: venous blood from 11 apparently healthy volunteers was collected (1 part 0.11 mol/L sodium citrate solution with 9 parts of blood) and centrifuged immediately at 2000×g for 30 minutes at 4° C. Plasma was removed, pooled and stored in aliquots at −70° C. until use.

Inhibitors: were dissolved in DMSO (10 mM stock solution) and diluted with distilled water to working solutions (the highest concentration 100 µM).

c) Method

Inhibitor (10 µL working solution, concentrations from 5 µM to 100 µM) and pooled plasma (90 µL) were incubated at 37° C. for 5 minutes and then Thromborel S (200 µL) was added. Clot formation was measured with a coagulometer in duplicate.

Enzyme Assay

The enzyme inhibitory effect of the compounds can be identified by determination of inhibition constant Ki. It denotes the degree of dissociation of the enzyme-inhibitor complex. Low dissociation constant means high potency of inhibitor. Ki can be determined during reaction of the enzyme with a specific chromogenic substrate which under hydrolysis by the enzyme develops color. Reaction in time is recorded by spectrophotometry and Ki is calculated from kinetic parameters (Vmax, Km, reaction rate).

1. Determination of Thrombin Ki a) Principle of Method

The ability of a compound to act as an inhibitor of human thrombin catalytic activity was assessed by determination of Ki.

b) Reagents

Buffer HBSA, pH 7.5 (10 mM Hepes, 150 mM NaCl, 0.1% w/v bovine serum albumin)

Substrate (S-2238: H-D-Phe-Pip-Arg-pNA HCl, 25 mg; Chromogenix): dissolved in distilled water to 1 mM concentration. (Km is 2.6 µM)

Human thrombin (308 NIH; Sigma): dissolved in saline to give a stock solution of 20 NIH/mL.

Inhibitors: were dissolved in DMSO (10 mM stock solution) and diluted with distilled water to working solutions (the highest final concentration of DMSO was 3%).

c) Method

A mixture of 50 µL of buffer, 50 µL of inhibitor in water (final concentrations from 10 to 100 µM) and 50 µL of thrombin (0.5 NIH U/mL f.c.) was incubated for 15 minutes at room temperature. The reaction was started with 50 µL of S-2238 (20 µM or 40 µM f.c.) and the absorbance of each sample at 405 nm (at 25° C.) was measured in triplicate every 10 seconds for a period of 15 minutes using a microtiter plate reader (Tecan Sunrise).

Thrombin activity was determined from the change in absorbance in the linear part of the velocity graph. Ki was calculated according to Cheng and Prussof (Biochem Pharmacol, 1973) where Ki is $IC_{50}/(1+S/Km)$. The Km for the substrate was determined under the test conditions with at least 6 substrate concentrations varying around Km and calculated with the non-linear regression programme Curve expert.

2. Determination of Trypsin Ki a) Principle

The ability of a compound to act as an inhibitor of trypsin catalytic activity was assessed by determination of Ki.

b) Reagents

Buffer: HBSA, pH 7.5 (10 mM Hepes, 150 mM NaCl, 0.1% w/v bovine serum albumin)

Substrate (S-2222: N-benzoyl-Ile-Glu-Gly-Arg-pNA HCl, 25 mg; Chromogenix): dissolved in distilled water to 2 mM concentration. (Km is 21 µM)

Trypsin (6000 E/mg prot.; Sigma): dissolved in distilled water to give a stock solution of 300 E/mL.

Inhibitors: were dissolved in DMSO (10 mM stock solution) and diluted with distilled water to working solution (the highest final concentration of DMSO was 10%).

c) Method

50 µL of buffer, 50 µL of test compound in water (final concentrations from 50 to 300 µM) and 50 µL of trypsin (3 mE/mL f.c.) were incubated for 15 minutes at room temperature. The reaction was started with 50 µL of S-2222 (50 µM or 100 µM f.c.) and the absorbance of each sample at 405 nm (at 25° C.) was measured in triplicates every 10 seconds for a period of 15 minutes using a microtiter plate reader (Tecan Sunrise).

Trypsin activity was determined from the change in absorbance in the linear part of velocity graph. Ki was calculated according to Cheng and Prussof (Biochem Pharmacol, 1973) where Ki is $IC_{50}/(1+S/Km)$. The Km for the substrate was determined under test conditions with at least 6 substrate concentrations varying around Km and calculated with the non-linear regression program Curve expert.

3. Selectivity to Thrombin

By the use of other serine protease like trypsin with the appropriate chromogenic substrate, selectivity of inhibitors with respect to thrombin was determined. Selectivity of an inhibitor is expressed as a ratio of Ki for trypsin to Ki for thrombin.

In vivo Assays

1. Stasis-Induced Thrombosis

Principle of Method

Using a combination of thrombogenic challenge (0.045 ng/kg of tissue factor) and stasis, compounds were tested for their abillity to affect thrombus formation in a venous thrombosis model in the rat.

Method

Thrombus formation by a combination of stasis and hypercoagulability was induced as described by Vogel et al. (Thromb. Res., 1989, 54, 399410). Male sprague-Dawley rats (250-300 g) were anaesthetized with sodium pentobarbitone (30 mg/kg, i.p.). The abdomen of the animals was surgically opened and after careful dissection, the vena cava was exposed and dissected free from surrounding tissue. Saline, or the various compounds were administered i.v. 5 min before thrombosis induction. Two loose sutures were prepared 0.7 cm apart on the inferior vena cava and all collateral veins were ligated. Human tissue factor (0.045 ng/kg, i.v.) was injected into the dorsal vein of the penis. Ten seconds after the end of the injection, stasis were established by tightening the two, firstly the proximal and then the distal. The abdominal cavity was provisionally closed and stasis was maintained for 20 minutes. The cavity was then reopened, the ligated segment was opened longitudinally and the thrombus formed was removed, rinsed, blotted on filter paper, dried overnight at 60° C. and weighed. Under these experimental conditions, control thrombus weight was 5.5±0.1 mg (n=15).

2. Bleeding Time

Principle of Method

The hemorrhagic risk associated to a treatment with selected compounds were determined using an experimental model of bleeding: transection of the tail of rats.

Method

Bleeding time was determined by transection of the tail, 2 mm from the tip, of phenobarbital-anaestetised rats (30 mg/kg i.p.). The compounds were injected i.v. at the indicated doses 5 min before tail transection. Blood was carefully blotted every 15 s on a filter paper. Haemostasis was considered to be achieved when no more blood stain was observed over 1 min.

EXAMPLES

The invention is further described by means of the following examples, but not in any limitative case:

Example 1 tert-Butyl 2-(3-cyanobenzyl)-2-[(4-methyl-1-piperidinyl)carbonyl]-1-hydrazinecarboxylate

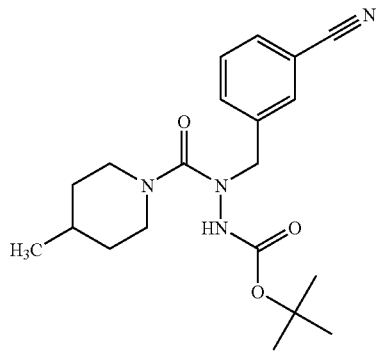

Triphosgene (2.296 g) was dissolved in 15 ml of anhydrous dichloromethane and cooled to −5° C. While stirring under argon atmosphere, a solution of N-1-(tert-butoxycarbonyl)-N-2-[(3-cyanophenyl)methyl]hydrazine (3.833 g) and N, N-diisopropylethylamine (4.040 ml) in 25 ml of dichloromethane was added dropwise. After addition, the reaction mixture was stirred for another 5 minutes, and a mixture of 4-methyl piperidine (1.836 ml) and N,N-diisopropylethylamine (4.040 ml) in 25 ml dichloromethane was then added at once and stirred at room temperature for another 20 minutes. The solvent was evaporated in vacuo and the residue was dissolved in 50 ml of ethyl acetate, washed with 25 ml of 5% citric acid, with 25 ml of 5% solution of NaHCO$_3$ and with 25 ml of brine. The organic phase was dried over MgSO$_4$, filtered and the filtrate evaporated under reduced pressure.

The resulting mixture was suspended in 20 ml of diethylether and 5 ml of hexane was added. The precipitate was filtered by suction.

Yield: 1.756 g (30.4%)

Melting range: 147-150° C.

IR (KBr, cm$^{-1}$): 3275.0, 2922.7, 2229.3, 1722.3, 1632.3, 1497.3, 1445.5, 1367.6, 1252.9, 1157.0, 979.2, 805.1, 736.2, 573.7

NMR (DMSO-d$_6$)): δ (ppm): 0.86 (d, J=6,4 Hz, 3H, CH$_3$), 0.90-1.05 (m, 2H, Pip-H$^{3',5'}$), 1.35 (s, 9H, Boc), 1.45-1.60 (m, 4H, Pip-H$^{3',5'}$), 2.60-2.75 (m, 2H, Pip-H$^{2,6}$), 3.70-3.85(m, 2H, Pip-H$^{2',6'}$), 4.52 (br s, 2H, CH$_2$), 7.58-7.66 (m, 1H, Bn-H$^5$), 7.79-7.85 (m, 1H, Bn-H$^6$), 7.93-8.05 (m, 2H, Bn-H$^{2,4}$), 11.05 (s, 1H, NH).

Molecular weight of C$_{20}$H$_{27}$ N$_4$ O$_3$: calculated: 372; found: 373 (MH$^+$)

Example 2

2-(3-Cyanobenzyl)-2-[(4-methyl-1-piperidinyl)carbonyl]hydrazinium Chloride

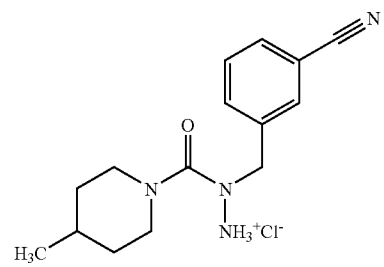

terc-butyl 2-(3-cyanobenzyl)-2-[(4-methyl-1-pyperidinyl)carbonyl]hydrazine carboxylate (1.173 mg) was dissolved in 30 ml of glacial acetic acid and HCl gas was bubbled through the solution for 20 minutes. The progress of the reaction was monitored by TLC. Glacial acetic acid was evaporated on a rotavapor, and diethylether was poured over the oily product. The liquid phase was removed, the resulting precipitate is dried at 50° C. and desiccated over NaOH for 24 hours.

Yield: 0.875 g (%) of the mixture

Melting range: 170-173° C.

IR (KBr, cm$^{-1}$): 3417.8, 2934.6, 2664.1, 2227.3, 1711.6, 1641.3, 1433.7, 1402.3, 1249.6, 1132.0, 1017.8

NMR (DMSO-d$_6$): δ (ppm): 0.92 (d, J=6,4 Hz, 3H, CH$_3$), 0.99-1.16 (m, 2H, Pip-H$^{3,5}$), 1.52-1.71 (m, 4H, Pip-H$^{3',5'}$), 2.90-3.05 (m, 2H, Pip-H$^{2,6}$), 3.80-3.95(m, 2H, Pip-H$^{2',6'}$), 4.62 (s, 2H, CH$_2$), 7.59-7.69 (m, 1H, Bn-H$^{4,5}$), 7.79-7.88 (m, 1H, Bn-H$^{2,6}$).

Molecular weight of C$_{14}$H$_{19}$ClN$_4$O: calculated: 294.78; found: 295(MH$^+$)

Example 3

N'-(3-Cyanobenzyl)-N'-[(4-methyl-1-piperidinyl)carbonyl]-2-naphthalenesulfonohydrazide

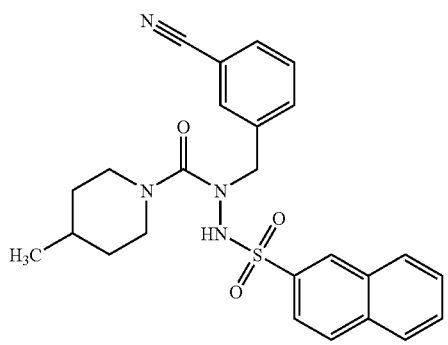

2-(3-cyanobenzyl)-2-[(4-methyl-1-pyperidinyl)carbonyl]hydrazine (0.870 g) was dissolved in 50 ml of dichloromethane, cooled to −5° C. and while stirring, 1.190 ml of triethylamine and 0.640 g of naphthalen-2-sulfonylchloride were added. The reaction mixture was stirred at −5° C. for 30 minutes and then at room temperature for another 24 hours. The solvent was evaporated under reduced pressure and 100 ml of ethyl acetate was added to the residue. In the separatory funnel it was washed twice with 50 ml of water, with 50 ml of 10% of citric acid and with 50 ml of brine. The organic phase was dried over $Na_2SO_4$, filtered and the filtrate was evaporated in vacuo. The resulting product was suspended in diethylether and the precipitate was filtered by suction. The precipitate was then recrystalized from ethanol and the crystals were filtered by suction.

Yield: 0.464 g (35.6%)

Melting range: 92-95° C.

IR (KBr, cm$^{-1}$): 3191.7, 2931.6, 2221.0, 1680.5, 1433.5, 1333.1, 1168.8, 857.9, 749.4, 692.2

$^1$H NMR (DMSO-$d_6$)): δ (ppm): 0.10-0.35 (m, 2H, Pip-H$^{3',3',5,5'}$), 0.47 (d, 3H, J=6.0 Hz, CH$_3$), 1.22-1.32 (m, 3H, Pip-H$^{3,3',4,4',5,5'}$), 2.30-2.45 (m, 1H, Pip-H$^{2,2'}$), 2.65-2.80 (m, 1H, Pip-H$^{6,6'}$), 3.45-3.65 (m, 2H, Pip-H$^{2,2',6,6'}$), 4,38 (br d, 2H, CH$_2$), 7.47-7.55 (m, 2H, Bn-H$^{5,6}$), 7.58-7.63 (m, 1H, Bn-H$^2$), 7.63-7.80 (m, 4H, Bn-H$^4$ in Nf-H$_{3,6,7}$), 8.02-8.18 (m, 3H, Nf-H$^{4,5,8}$), 8.43 (s, 1H, Nf-H$^1$), 9.60 (s, 1H, NH). Two sets of signals Molecular weight of $C_{25}H_{26}N_4O_3S$: calculated: 462.6; found: 463 (MH$^+$)

Example 4

N'-Hydroxy-3-{[1-[(4-methyl-1-piperidinyl)carbonyl]-2-(2-naphthylsulfonyl)hydrazino]methyl}benzenecarboximidamide

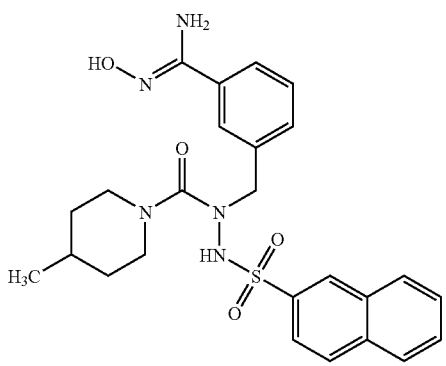

N'-(3-cyanobenzyl)-N'-[(4-metyl-1-pyperidinyl)carbonyl]-2-naphthalene sulfonohydrazide (0.223 g) was suspended in 20 ml of anhydrous ethanol under argon atmosphere and 0.032 g of hydroxylamine was added. The reaction mixture was heated at reflux temperature for 24 hours and evaporated under reduced pressure. The resulting product was purified by column chromatography (eluent: chloroform/methanol=9/1) to yield white crystals.

Yield: 0.215 g (38%)

Melting range: 169-173° C.

IR (KBr, cm$^{-1}$): 3365.8, 3194.6, 2943.8, 2864.7, 1652.6, 1447.5, 1332.2, 1169.3, 1076.1, 756.2, 700.3, 553.2

$^1$H-NMR (DMSO-$d_6$): δ (ppm): 0.01-0.36 (m, 2H, Pip-H$^{3,5}$), 0.44 (d, 3H, J=6.4 Hz, CH$_3$), 1.15-1.27 (m, 3H, Pip-H$^{3,4,5}$), 2.27-2.42 (m, 1H, Pip-H$^2$), 2.56-2.75 (m, 1H, Pip-H$^6$), 3.45-3.63 (m, 2H, Pip-H$^{2,6}$), 4.35 (br d, 2H, CH$_2$), 7.14 (d, 1H, J=7.9, Bn-H$^4$), 7.25-7.40 (m, 1H, Bn-H$^5$), 7.48-7.59 (m, 2H, Bn-H$^{2,6}$), 7.63-7.81 (m, 3H, Nf-H$^{3,6,7}$), 8.02-8.19 (m, 3H, Nf-H$^{4,5,8}$), 8.46 (s, 1H, Nf-H$^1$), 9.40 (s, 1H, NH), 9.78 (s, 1H, OH).

Molecular weight of $C_{25}H_{30}N_5O_4S$: calculated: 495.6; found: 496 (MH$^+$)

Example 5

Imino(3{[1-[(4-methyl-1-piperidinyl)carbonyl]-2-(2-naphthylsulfonyl)hydrazino]methyl}phenyl)methanaminium Chloride

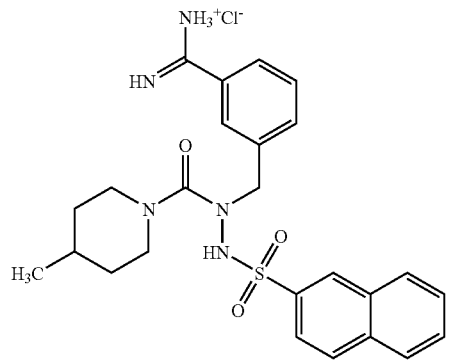

N'-(3-cyanobenzyl)-N'-[(4-methyl-1-pyperidinyl)carbonyl]-2-naphthalene sulfonohydrazide (0.200 g) was suspended in 10 ml of ethanol, cooled in an ice bath and HCl was bubbled into the suspension for 30 minutes. The mixture was stirred at room temperature for 4 hours and then the solvent was evaporated under reduced pressure. The solid residue was washed with isopropyl ether and filtered by suction. The resulting precipitate was dissolved in 10 ml ethanol and ammonium acetate (0.092 g) was added. The resulting mixture was stirred at room temperature for 20 hours and then HCl was passed through the solution for 30 minutes. After 24 hours the white precipitate was formed which was filtered by suction.

Yield: 50.4 mg (52%)

Melting range: 148-152° C.

IR (KBr, cm$^{-1}$): 3396.1, 3101.7, 2945.8, 1669.1, 1435.8, 1335.9, 1165.9, 1072.4, 749.4, 668.4

$^1$H-NMR (DMSO-$d_6$): δ (ppm): 0.01-0.40 (m, 2H, Pip-H$^{3,5}$), 0.47 (d, 3H, J=6.4 Hz, CH$_3$), 1.15-1.29 (m, 3H, Pip-H$^{3,4,5}$), 2.27-2.42 (m, 1H, Pip-H$^2$), 2.56-2.75 (m, 1H, Pip-H$^6$), 3.45-3.60 (m, 2H, Pip-H$^{2,6}$), 4.41 (br d, 2H, CH$_2$), 7.14 (d, 1H, J=7.9, Bn-H$^4$), 7.25-7.40 (m, 1H, Bn-H$^5$), 7.48-7.59 (m, 2H, Bn-H$^{2,6}$), 7.63-7.81 (m, 3H, Nf-H$^{3,6,7}$), 8.02-8.19 (m, 3H, Nf-H$^{4,5,8}$), 8.46 (s, 1H, Nf-H$^1$), 9.40 (s, 1H, NH).

Molecular weight of $C_{24}H_{27}N_5O_3S$ (free base): calculated: 465.57; found: 466 (MH$^+$)

Example 6 tert-Butyl 2-(3-cyanobenzylidene)-1-hydrazinecarboxylate

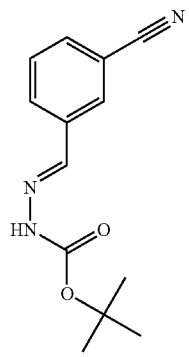

3-Cyanobenzaldehyde (40.0 mmol) suspended in EtOH (100 mL) was added to a stirred solution of tert-butylcarbazate (40.0 mmol) in EtOH. The mixture was heated at reflux temperature and after 4 h the EtOH was partially evaporated in vacuo. Water (100 mL) was added and the precipitated product was collected by filtration and washed with diethylether to give tert-butyl 2-(3-cyanobenzylidene)-1-hydrazinecarboxylate as a white solid.

Yield: 77%.
MP: 115-158° C.
IR (KBr): 3297, 2977, 2232, 1703, 1530, 1477, 1376, 1248, 1160, 1061, 941, 865 cm$^{-1}$.
MS (FAB): MH$^+$=246.
$^1$H NMR (300 MHz CDCl$_3$): 1.55 (s, 9H, Boc-H), 7.55 (m, 2H, Bn-H), 7.93 (m, 3H, Bn-H in CH), 8.24 (s, 1H, NH).
Elemental analysis: calculated for C$_{13}$H$_{15}$N$_3$O$_2$: C, 63.66; H, 6.16; N, 17.13, found C, 63.38; H, 6.18; N, 17.09.

Example 7 tert-Butyl 2-(3-cyanobenzyl)-1-hydrazinecarboxylate

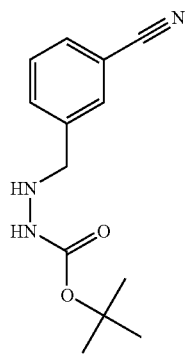

tert-Butyl 2-(3-cyanobenzylidene)-1-hydrazinecarboxylate (60.0 mmol) was dissolved in MeOH (250 mL) and 10% Pd/C (10 w/w %) was added. The mixture was hydrogenated for 6 h. The catalyst was filtered off and the filtrate was evaporated in vacuo to yield oily tert-butyl 2-(3-cyanobenzyl)-1-hydrazinecarboxylate which crystallized overnight.

Yield: 95%.
MP: 75-80° C.
IR (KBr): 3368, 2980, 2226, 1679, 1482, 1366, 1286, 1166, 793 cm$^{-1}$
MS (FAB): MH$^+$=248.
$^1$H NMR (300 MHz CDCl$_3$): 1.47 (s, 9H, Boc-H), 4.04 (br s, 2H, CH$_2$), 4.28 (br s, 1H, NH), 6.09 (br s, 1H, NH), 7.12-7.41(m, 4H, Bn-H).
Elemental analysis: calculated for C$_{13}$H$_{17}$N$_3$O$_2$·¼ H$_2$O: C, 62.01; H, 7.00; N. 16.69; found C, 61.90; H, 7.22; N, 16.69.

Example 8 tert-Butyl 2-(3-cyanobenzyl)-2-[(2-methyl-1-piperidinyl)carbonyl]-1-hydrazinecarboxylate

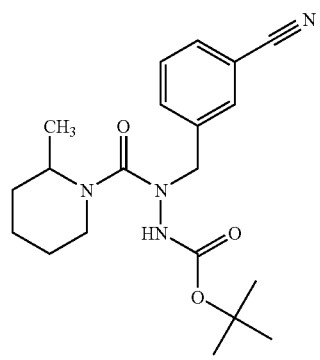

The product was prepared from tert-butyl 2-(3-cyanobenzyl)-1-hydrazinecarboxylate and 2-methylpiperidine using the procedure described in EXAMPLE 1.

Yield: 42%.
MP: oil
IR (KBr): 3271, 2941, 2230, 1725, 1644, 1428 cm$^{-1}$.
MS (FAB): MH$^+$=373.
$^1$H NMR (300 MHz, CDCl$_3$): 1.22 (d, J=6,8 Hz, 3H, CH$_3$), 1.45 (s, 9H, Boc), 1.45-1.79 (m, 5H, Pip-H), 2.97-3.10 (m, 1H, Pip-H), 3.44-3.54 (m, 1H, Pip-H), 3.63-3.76 (m, 1H, Pip-H), 4.18-4.32 (m, 1H, Pip-H), 4.48 (s, 2H, CH$_2$), 6.30 (s, 1H, NH), 7.46 (t, J=7.9 Hz, 1H, Bn-H), 7.56-7.67 (m, 3H, Bn-H).

Example 9

2-(3-Cyanobenzyl)-2-[(2-methyl-1-piperidinyl)carbonyl] hydrazinium Chloride

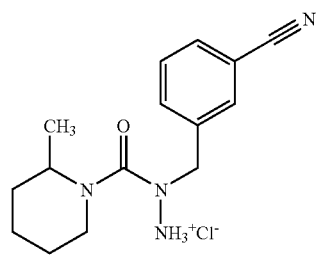

The product was prepared from tert-butyl 2-(3-cyanobenzyl)-2-[(2-methyl-1-piperidinyl)carbonyl]-1-hydrazinecarboxylate using the procedure described in EXAMPLE 2

Yield: 91%.
MP: 135-137° C.
IR (KBr): 3429, 2949, 2229, 2708, 2230, 1694, 1526, 1420 cm$^{-1}$.
MS (FAB): MH$^+$=273.
$^1$H NMR (300 MHz, CDCl$_3$): 1.23 (d, J=6,8 Hz, 3H, CH$_3$), 1.40-1.51 (m, 1H, Pip-H) 1.52-1.79 (m, 5H, Pip-H), 2.98-3.10 (m 1H, Pip-H), 3.60-3.79 (m, 1H, Pip-H), 4.25-4.38 8 (m, 1H, Pip-H), 4.64 (s, 2H, CH$_2$), 7.53 (t, J=7.9 Hz, 1H, Bn-H), 7.61-7.76 (m, 3H, Bn-H), 9.60 (br s, 2H, NH$_2$).

Example 10 tert-Butyl 2-(1-azepanylcarbonyl)-2-(3-cyanobenzyl)-1-hydrazinecarboxylate

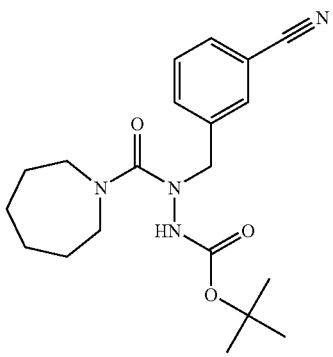

The product was prepared from tert-butyl 2-(3-cyanobenzyl)-1-hydrazinecarboxylate and azepane using the procedure described in EXAMPLE 1.

Yield: 63%.
MP: oil.
IR (KBr): 3287, 2925, 2223, 1726, 1634 cm$^{-1}$.
MS (FAB): MH$^+$=373.
$^1$H NMR (300 MHz, CDCl$_3$): 1.45 (s, 9H, Boc), 1.53-1.62 (m, 4H, Pip-H$^{4,5}$), 1.69-1.80 (m, 4H, Pip-H$^{3,6}$), 3.39-3.46 (m, 4H, Pip-H$^{2,7}$), 4.50 (s, 2H, CH$_2$), 6.25 (br s, 1H, NH), 7.45 (t, J=7.9 Hz, 1H, Bn-H), 7.56-7.69 (m, 3H, Bn-H).

Example 11

2-(1-Azepanylcarbonyl)-2-(3-cyanobenzyl)hydrazinium Chloride

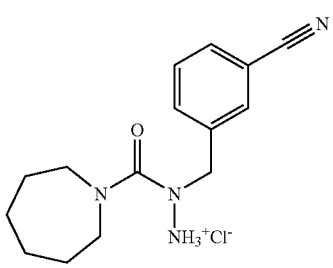

The product was prepared from tert-butyl 2-(1-azepanyl-carbonyl)-2-(3-cyanobenzyl)-1-hydrazinecarboxylate using the procedure described in EXAMPLE 2.

Yield: 66%.
MP: oil.
IR (KBr): 2926, 2702, 2230 1703, 1521 cm$^{-1}$.
MS (FAB): MH$^+$=273.
$^1$H NMR (300 MHz, CDCl$_3$): 1.53-1.64 (m, 4H, Pip-H$^{4,5}$), 1.65-1.81 (m, 4H, Pip-H$^{3,6}$), 3.38-3.46 (m, 4H, Pip-H$^{2,7}$), 4.70 (s, 2H, CH$_2$), 7.48-7.64 (m, 2H, Bn-H), 7.69-7.80 (m, 2H, Bn-H), 9.60 (br s, 2H, NH$_2$).

Example 12

N'-(3-cyanobenzyl)-N'-[(2-methyl-1-piperidinyl)carbonyl]-2-naphthalenesulfonohydrazide

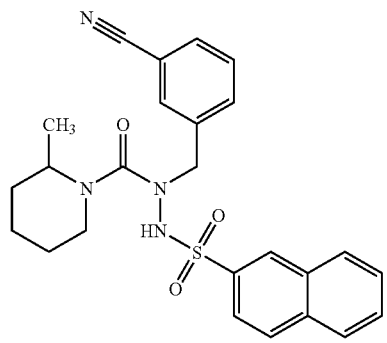

The product was prepared from 2-(3-cyanobenzyl)-2-[(2-methyl-1-piperidinyl)carbonyl]hydrazinium chloride and naphthalene-2-sulfonyl chloride using the procedure described in EXAMPLE 3.

Yield: 14%.
MP: 116-119° C.
IR (KBr): 3231, 2943, 2227, 1653 cm$^{-1}$.
MS (FAB): MH$^+$=273.
$^1$H NMR (300 MHz CDCl$_3$): 0.35-0.55 (m, 2H, Pip-H), 0.75-0.90 (m, 2H, Pip-H), 1.03-1.45 (m, 6H, Pip-H in CH$_3$), 2.54-2.70 in 2.75-2.95 (m, 1H, Pip-H) 3.50-3.75 in 3.75-4.00 (m, 1H, Pip-H), 4.31 (br d, 2H, CH$_2$), 7.35-7.70 (m, 7H, Bn-H in Nph-H), 7.75-7.85(m, 1H, Nph-H), 7.86-8.00 (m, 3H, Nph-H), 8.42 (s, 1H, Nph-H), (two sets of signals).

Elemental analysis: calculated for C$_{25}$H$_{26}$ N$_4$ O$_3$ S: C, 64.91; H, 5.67; N, 12.11; found: C, 65.07; H, 5.58; N, 11.93.

Example 13

N'-hydroxy-3-{[1-[(2-methyl-1-piperidinyl)carbonyl]-2-(2-naphthylsulfonyl)hydrazino]methyl}benzenecarboximidamide

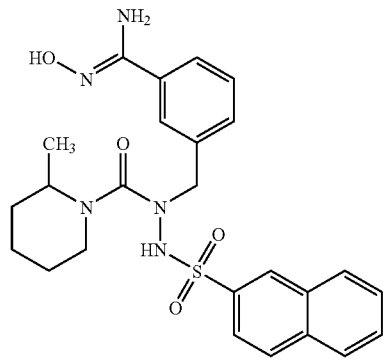

The product was prepared from N'-(3-cyanobenzyl)-N'-[(2-methyl-1-piperidinyl)carbonyl]-2-naphthalenesulfonohydrazide using the procedure described in EXAMPLE 4.
Yield: 48%.
MP: 101-103° C.
IR (KBr): =3370, 2932, 1651 cm$^{-1}$.
MS (FAB): MH$^+$=496.

Example 14

N'-(3-Cyanobenzyl)-6-methoxy-N'-[(2-methyl-1-piperidinyl)carbonyl]-2-naphthalenesulfonohydrazide

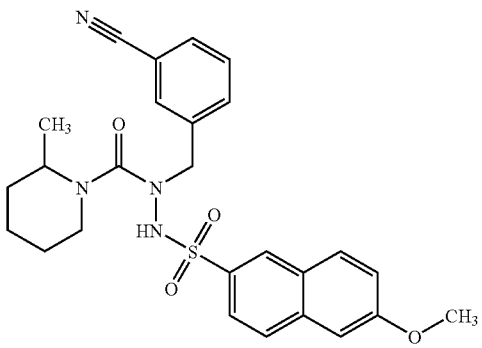

The product was prepared from 2-(3-cyanobenzyl)-2-[(2-methyl-1-piperidinyl)carbonyl]hydrazinium chloride and 6-methoxy-2-naphthalenesulfonyl chloride using the procedure described in EXAMPLE 3.
Yield: 26%.
MP: 169-173° C.
IR (KBr): 3172, 2934, 2229, 1671, 1623 cm$^{-1}$.
MS (FAB): MH$^+$=493273.
$^1$H NMR (300 MHz, CDCl$_3$): 0.47-0.60 (m, 2H, Pip-H), 0.79-0.92 (m, 2H, Pip-H), 1.12-1.50 (m, 6H, Pip-H in CH$_3$), 2.50-2.75 in 2.80-3.15 (m, 1H, Pip-H), 3.55-3.76 in 3.80-3.95 (m, 1H, Pip-H), 3.95 8s, 3H, OCH$_3$); 2.55-2.74 (m, 1H, Pip-H), 3.45-3.65 (m, 2H, Pip-H), 3.84 (s, 3H, CH$_3$), 4.32 (br d, 2H, CH$_2$), 7.28-7.33 (m, 1H, Nph-H), 7.44-7.60 (m, 5H, Bn-H and Nph-H), 7.75-7.88 (m, 3H, Nph-H), 8.34 (d, 1H, J=1.88 Hz, Nph-H).

Example 15

N'-Hydroxy-3-({2-[(6-methoxy-2-naphthyl)sulfonyl]-1-[(2-methyl-1-piperidinyl)carbonyl]hydrazino}methyl)benzenecarboximidamide

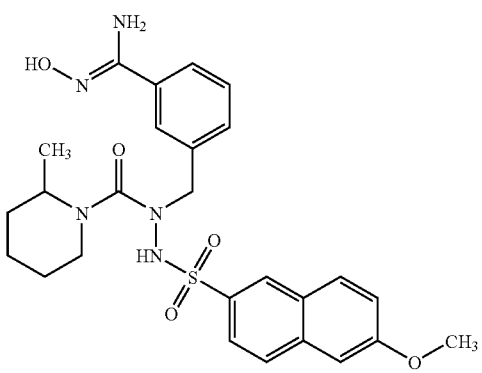

The product was prepared from N'-(3-Cyanobenzyl)-6-methoxy-N'-[(2-methyl-1-piperidinyl)carbonyl]-2-naphthalenesulfonohydrazide using the procedure described in EXAMPLE 4.
Yield: 45%.
MP: 172-175° C.
IR (KBr): 3368, 2937, 1647, 1160 cm$^{-1}$.
MS (FAB): MH$^+$=526.
$^1$H NMR (300 MHz, CDCl$_3$): 0.35-0.50 (m, 2H, Pip-H), 0.79-1.00 (m, 2H, Pip-H), 1.12-1.50 (m, 6H, Pip-H in CH$_3$), 2.40-2.75 in 2.80-3.00 (m, 1H, Pip-H), 3.55-3.76 in 3.80-3.95 (m, 1H, Pip-H), 3.95 (s, 3H, OCH$_3$); 4.35 (br d, 2H, CH$_2$), 5.04 (s, 2H, NH$_2$), 7.15-7.65 (m, 6H, Nph-H in Bn-H), 7.74-7.87 (m, 3H, Nph-H), 8.34 (s, 1H, Nph-H).
Elemental analysis: calculated for C$_{26}$H$_{31}$N$_5$O$_5$S·EtOH: C, 58.83; H, 6.52; N, 12.25; found: C, 59.41; H, 5.96; N, 12.09.

Example 16

N'-(3-Cyanobenzyl)-6-methoxy-N'-[(4-methyl-1-piperidinyl)carbonyl]-2-naphthalenesulfonohydrazide

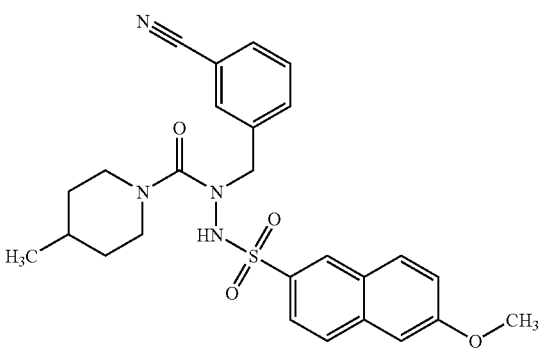

The product was prepared from 2-(3-cyanobenzyl)-2-[(4-methyl-1-piperidinyl)carbonyl]hydrazinium chloride using the procedure described in EXAMPLE 3.
Yield: 50%.
MP: 169-173° C.
IR (KBr): 3168, 2932, 2232, 1671 cm$^{-1}$.
MS (FAB): MH$^+$=493.
$^1$H NMR (300 MHz, DMSO-d$_6$): 0.15-0.40 (m, 2H, Pip-H), 0.53 (d, 3H, J=6.0 Hz, CH$_3$), 1.25-1.39 (m, 3H, Pip-H), 2.25-2.38 (m, 1H, Pip-H), 2.55-2.74 (m, 1H, Pip-H), 3.45-3.65 (m, 2H, Pip-H), 3.84 (s, 3H, CH$_3$), 4.32 (br d, 2H, CH$_2$), 7.28-7.33 (m, 1H, Nph-H), 7.44-7.54 (m, 3H, Bn-H and Nph-H), 7.60 (d, 1H, J=1.88 Hz, Bn-H), 7.60-7.76 (m, 2H, Bn-H and Nph-H), 7.94 (d, 1H, J=8.66 Hz, Nph-H), 8.05 (d, 1H, J=8.66 Hz, Nph-H), 8.34 (d, 1H, J=1.88 Hz, Nph-H$^1$), 9.46 (s, 1H, NH).

Example 17

N'-Hydroxy-3-({2-[(6-methoxy-2-naphthyl)sulfonyl]-1-[(4-methyl-1-piperidinyl)carbonyl]hydrazino}methyl)benzenecarboximidamide The product was prepared from N'-(3-cyanobenzyl)-6-methoxy-NV-(4-methyl-1-piperidinyl)carbonyl]-2-naphthalenesulfonohydrazide using the procedure described in EXAMPLE 4.

Yield: 36%.
MP: 154-156° C.
IR (KBr): 3473, 3365, 2950, 1646 cm$^{-1}$.
MS (FAB): MH$^+$=526
$^1$H NMR (300 MHz, CDCl$_3$): 0.30 (br d, 3H, Pip-H), 0.58 (d, 3H, J=6.0 Hz, CH$_3$), 1.26 (br d, 3H, Pip-H), 2.45 (br s, 1H, Pip-H), 2.63 (br d, 1H, Pip-H), 3.74 (br d, 2H, Pip-H), 3.97 (s, 3H, OCH$_3$), 4.34 (br d, 2H, CH$_2$), 4.94 (s, 2H, NH$_2$) 7.17-7.35 (m, 4H, Nph-H and Bn-H), 7.49-7.55 (m, 2H, Bn-H), 7.77-7.89 (m, 4H, Bn-H and Nph-H), 8.35 (m, 1H, Bn-H). 8.65 (br s, 1H, NH), 9.02 (s, 1H, OH).

Example 18

Imino[3-({2-[(6-methoxy-2-naphthyl)sulfonyl]-1-[(4-methyl-1-piperidinyl)carbonyl]hydrazino}methyl)phenyl]methanaminium Chloride The product was prepared from N'-(3-cyanobenzyl)-6-methoxy-N'-[(4-methyl-1-piperidinyl)carbonyl]-2-naphthalenesulfonohydrazide using the procedure described in EXAMPLE 5.

Yield: 26%.
MP: 151-154° C.
IR (KBr): 3054, 1677, 1624 cm$^{-1}$.
MS (FAB): MH$^+$=510.
$^1$H NMR (300 MHz, CDCl$_3$): 0.28 (br d, 3H, Pip-H), 0.54 (d, 3H, J=6.0 Hz, CH$_3$), 1.27 (br d, 3H, Pip-H), 2.45 (br s, 1H, Pip-H), 2.64 (br s, 1H, Pip-H), 3.66 (br s, 2H, Pip-H), 3.95 (s, 3H, OCH$_3$), 4.32 (m, 2H, CH$_2$), 7.16-7.28 (m, 2H, Nph-H), 7.36-7.40 (m, 2H, Bn-H$^{2,6}$), 7.73-7.87 (m, 4H, Bn-H$_5$ and Nph-H), 7.95 (m, 1H, Bn-H$^4$), 8.78 (br s, 2H, NH$_2$), 8.16 (br s, 2H, NH$_2$).

Example 19

N'-(1-Azepanylcarbonyl)-N'-(3-cyanobenzyl)-2-naphthalenesulfonohydrazide

The product was prepared from N'-(1-azepanylcarbonyl)-N'-(3-cyanobenzyl)-2-naphthalenesulfonohydrazide and naphthalene-2-sulfonyl chloride using the procedure described in EXAMPLE 3.

Yield: 43%.
MP: 128-130° C.
IR (KBr): 3190, 2942, 2223, 1674 cm$^{-1}$.
MS (FAB): MH$^+$=463.
$^1$H NMR (300 MHz, DMSO-d$_6$): 0.63-1.40 (m, 8H, Pip-H$^{3,4,5,6}$), 2.90-3.20 (m, 4H, Pip-H$^{2,7}$), 4.35 (br d, 2H, CH$_2$), 7.45-5.55 (m, 2H, Nph-H in Bn-H), 7.50-7-75 (m, 5H, Nph-H in Bn-H), 8.02-8.15 (m, 3H, Nph-H), 8.45 (s, 1H, Nph-H), 9.56 (s, 1H, NH).

Elemental analysis: calculated for za C$_{25}$H$_{26}$ N$_4$ O$_3$ S: C, 64.91; H, 5.67; N, 12.11; found: C, 64.65; H, 5.78; N, 12.10.

Example 20

3{[-(1-Azepanylcarbonyl)-2-(2-naphthylsulfonyl)hydrazino]methyl}-N'-hydroxybenzenecarboximidamide The product was prepared from N'-(1-azepanylcarbonyl)-N'-(3-cyanobenzyl)-2-naphthalenesulfonohydrazide using the procedure described in EXAMPLE 4.

Yield: 79%.
MP: 152-155° C.
IR (KBr): 3365, 2924, 1646 cm$^{-1}$.
MS (FAB): MH$^+$=496.
$^1$H NMR (300 MHz, DMSO-d$_6$): 0.65-1.40 (m, 8H, Pip-H$^{3,4,5,6}$), 2.90-3.20 (m, 4H, Pip-H$^{2,7}$), 4.34 (br d, 2H, CH$_2$), 5.87 (br s, 2H, NH$_2$), 7.45-5.55 (m, 2H, Nph-H in Bn-H), 7.50-7-75 (m, 5H, Nph-H in Bn-H), 8.02-8.15 (m, 3H, Nph-H), 8.45 (s, 1H, Nph-H), 9.35 (br d, 1H, NH), 9.67 (br s, 1H, OH).

Example 21

(3{[1-(1-Azepanylcarbonyl)-2-(2-naphthylsulfonyl)hydrazino]methyl}phenyl)(imino)methanaminium Chloride

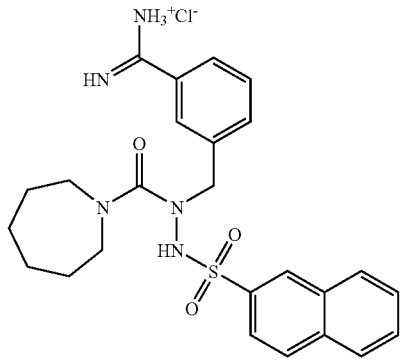

The product was prepared from N'-(1-azepanylcarbonyl)-N'-(3-cyanobenzyl)-2-naphthalenesulfonohydrazide using the procedure described in EXAMPLE 5.

Yield: 36%.
MP: 151-154° C.
IR (KBr): 3374, 3054, 2926, 1654, 1420, 1160 cm$^1$.
MS (FAB): MH$^+$=480.
$^1$H NMR (300 DMSO-d$_6$): 0.60-1.45 (m, 8H, Pip-H$^{3,4,5,6}$), 2.90-3.20 (m, 4H, Pip-H$^{2,7}$), 4.40 (br d, 2H, CH$_2$), 7.44 (d, J=8,3 Hz, 2H, Bn-H 2,6), 7.62-7.80 (m, 5H, Bn-H$^{3,5}$ in Nph-H), 8.02-8.18 (m, 3H, Nph-H), 8.45 (s, 1H, Nph-H), 9.09 (s, 2H, NH$_2$), 9.35 (s, 1H, NH)

Example 22

N'-(1-Azepanylcarbonyl)-N'-(3-cyanobenzyl)-6-methoxy-2-naphthalenesulfonohydrazide

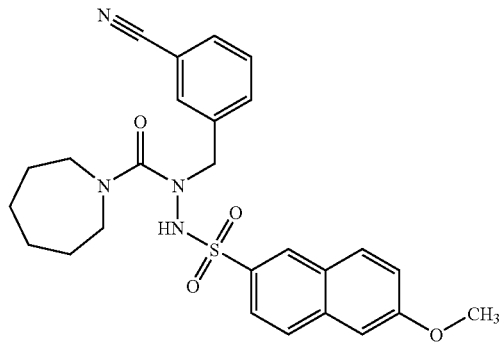

The product was prepared from 2-(3-cyanobenzyl)-2-[(4-methyl-1-piperidinyl)carbonyl]hydrazinium chloride using the procedure described in EXAMPLE 3.

Yield: 15%.
MP: 128-130° C.
IR (KBr): 3169, 2939, 2229, 1670 cm$^{-1}$.
MS (FAB): MH$^+$=493.
$^1$H NMR (300 MHz, DMSO-d$_6$): 0.65-1.50 (m, 8H, Pip-H$^{3,4,5,6}$), 2.85-3.20 (m, 4H, Pip-H$^{2,7}$), 3.91 (s, 3H, OCH$_3$) 4.35 (br d, 2H, CH$_2$), 7.28-7.32 (m, 1H, Bn-H), 7.42-7.52 (m, 3H, Bn-H in Nph-H), 7.60 (br s, 1H, Nph-H), 7.66-7.71 (m, 2H, Nph-H), 7.92 (d, 1H, J=8.7, Nph-H), 8.04 (d, 1H, J=8.7, Nph-H), 8.33 (d, 1H, J=1.5, Nph-H), 9.44 (s, 1H, NH).

Elemental analysis: calculated for C$_{26}$H$_{28}$ N$_4$ O$_4$ S: C, 63.14; H, 6.11; N, 11.33; found: C, 63.26; H, 5.87; N, 11.06.

Example 23

3-({1-(1-Azepanylcarbonyl)-2-[(6-methoxy-2-naphthyl)sulfonyl]hydrazino}methyl)-N'-hydroxybenzenecarboximidamide

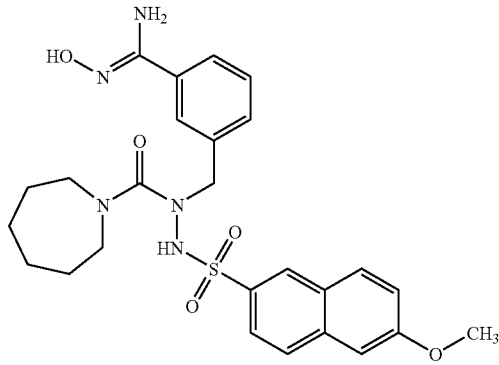

The product was prepared from IV-(1-azepanylcarbonyl)-N'-(3-cyanobenzyl)-6-methoxy-2-naphthalenesulfonohydrazide using the procedure described in EXAMPLE 4.

Yield: 24%.
MP: 173-175° C.
IR (KBr): 3459, 3368, 2932, 1648, cm$^{-1}$.
MS (FAB): MH$^+$=526.
$^1$H NMR (300 MHz, CDCl$_3$): 0.65-1.50 (m, 8H, Pip-H$^{3,4,5,6}$), 2.85-3.20 (m, 4H, Pip-H$^{2,7}$), 3.97 (s, 3H, OCH$_3$) 4.35 (s, 2H, CH$_2$), 4.95, (s, 1H, NH) 7.28-7.32 (m, 1H, Bn-H), 7.42-7.52 (m, 3H, Bn-H in Nph-H), 7.60 (br s, 1H, Nph-H), 7.66-7.71 (m, 2H, Nph-H), 7.92 (d, 1H, J=8.7 Hz, Nph-H), 8.04 (d, 1H, J=8.7 Hz, Nph-H), 8.33 (d, 1H, J=1.5 Hz, Nph-H), 8.10 (br s, 1H, NH), 8.35 (s, 1H, OH).

Elemental analysis: calculated for C$_{26}$H$_{31}$N$_5$ O$_5$ S: C, 59.18; H, 6.30; N, 13.27; found: C, 59.68; H, 6.16; N, 12.88.

Example 24

[3-({1-(1-Azepanylcarbonyl)-2-[(6-methoxy-2-naphthyl)sulfonyl]hydrazino}methyl)phenyl](imino)methanaminium Chloride

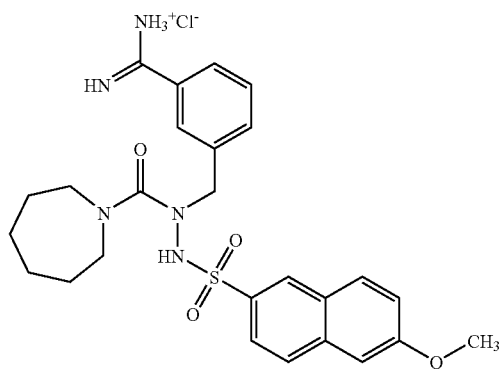

The product was prepared from N'-(1-azepanylcarbonyl)-N'-(3-cyanobenzyl)-6-methoxy-2-naphthalenesulfonohydrazide using the procedure described in EXAMPLE 5.

Yield: 21%.

MP: 151-154° C.

IR (KBr): 3057, 2929, 1677, 1623, 1474, 1157 cm$^{-1}$.

MS (FAB): MH$^+$=510.

$^1$H NMR (300 MHz CDCl$_3$): 0.65-1.40 (m, 8H, Pip-H$^{3,4,5,6}$), 2.95-3.20 (m, 4H, Pip-H$^{2,7}$), 3.97 (s, 3H, OCH$_3$) 4.35 (br s, 2H, CH$_2$), 7.44 (d, J=8,3 Hz, 2H, Bn-H$^{2,6}$), 7.62-7.80 (m, 5H, Bn-H$^{3,5}$ in Nph-H), 8.02-8.18 (m, 3H, Nph-H), 8.45 (s, 1H, Nph-H), 9.03 (s, 2H, NH$_2$), 9.35 (s, 2H, NH$_2$).

Results of Biological in Vitro Testing for Selected Compounds

| | Ki thrombin (μM) | Ki trypsin (μM) | Ki trypsin/ Ki thrombin | aPTT (μM) | PT (μM) | TT (μM) |
|---|---|---|---|---|---|---|
| 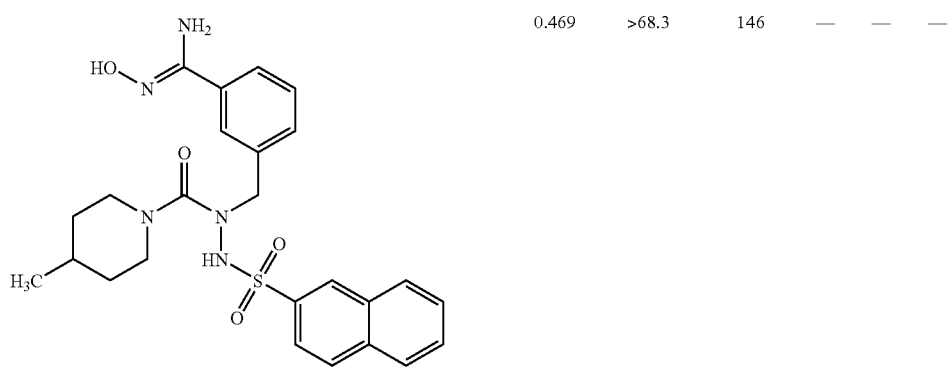 | 0.469 | >68.3 | 146 | — | — | — |
| 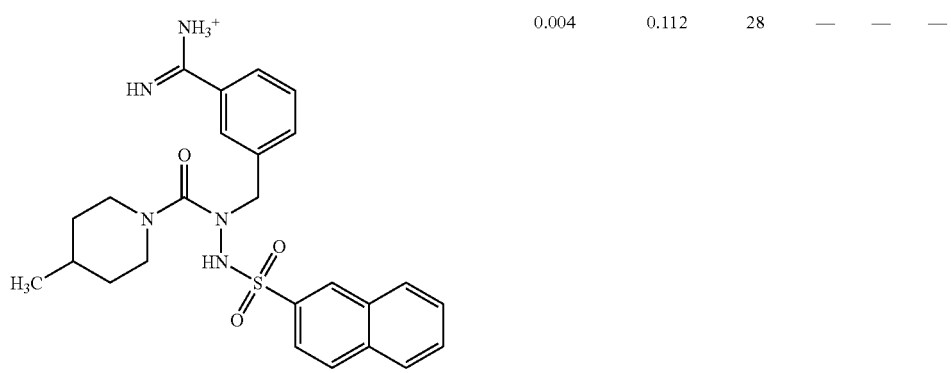 | 0.004 | 0.112 | 28 | — | — | — |

-continued
| | Ki thrombin (μM) | Ki trypsin (μM) | Ki trypsin/ Ki thrombin | aPTT (μM) | PT (μM) | TT (μM) |
|---|---|---|---|---|---|---|
| 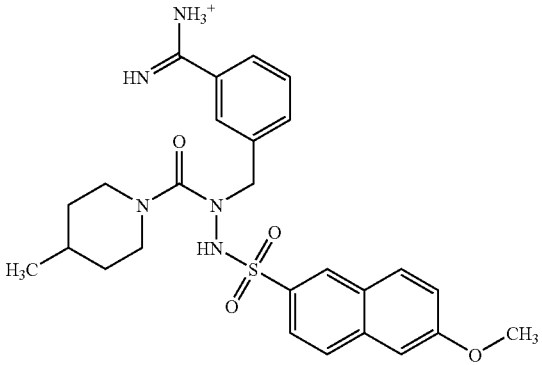 | 0.011 | — | — | 2.1 | 2.7 | 2.0 |
| 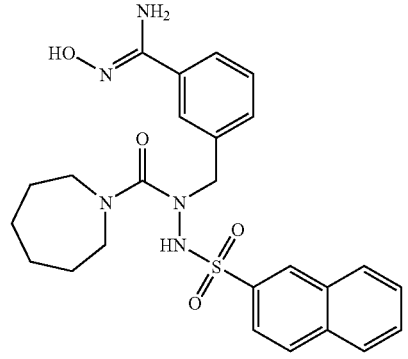 | 0.594 | 32.236 | 54 | — | — | — |
| 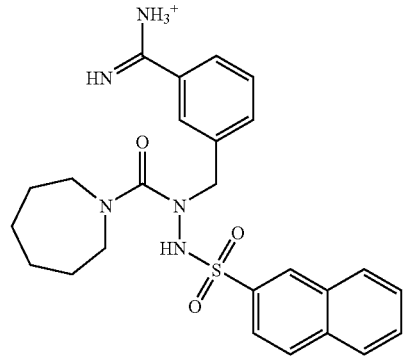 | 0.005 | 0.143 | 29 | — | — | — |
| 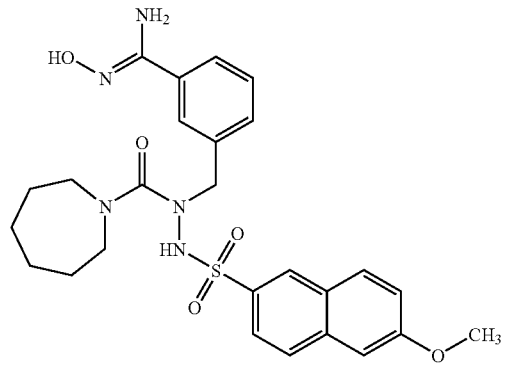 | 0.61 | 17.945 | 29 | — | — | — |

| | Ki thrombin (μM) | Ki trypsin (μM) | Ki trypsin/ Ki thrombin | aPTT (μM) | PT (μM) | TT (μM) |
|---|---|---|---|---|---|---|
| 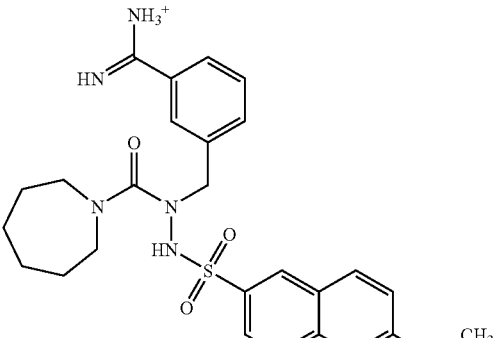 | 0.009 | 0.053 | 5.84 | — | — | — |
Example 27
Results of Biological in Vivo Testing for Selected Compounds
| | Stasis-induced thrombosis (ED$_{50}$ ± SD – mg/kg) | Bleeding (fold increase at 1 mg/kg) |
|---|---|---|
| 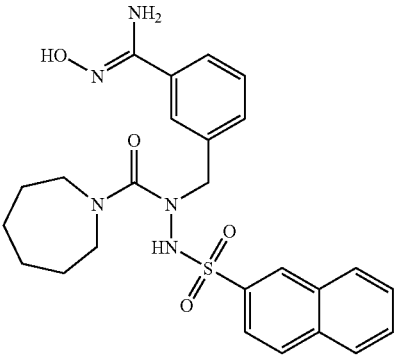 | 290 ± 11 | 3.3 |
| 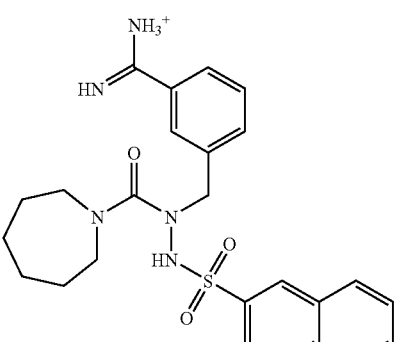 | 70 ± 5 | 9.4 |

The invention claimed is:

1. The compound of the formula I

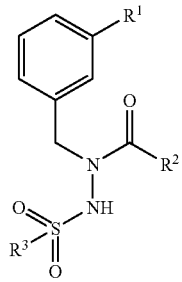

wherein
R¹ represents a residue of the formula

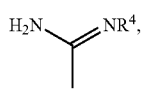

wherein R⁴ is selected from the group consisting of H, alkyl ($C_1$-$C_3$), OH, O-alkyl ($C_1$-$C_3$), and NH2;
R² is

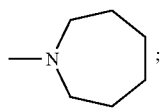

R³ is selected, from the group consisting of a residue of the formula

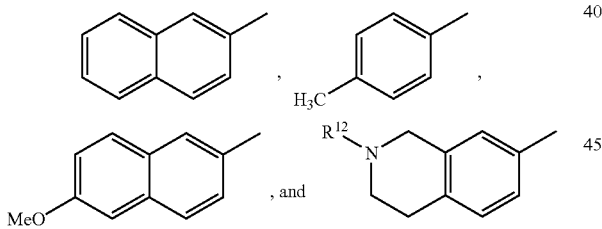

wherein $R^{12}$ is selected from the group consisting of H, $H_3C$-, and acetyl and pharmaceutically acceptable salts thereof.

2. A compound as claimed in preceding claim 1 wherein R³ represents a group selected from:

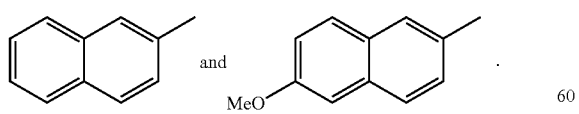

3. A compound as claimed in claim 1 wherein said compound is selected from the group consisting of:

3-{[1-(1-Azepanylcarbonyl)-2-(2-naphthylsulfonyl)hydrazino]methyl}-N'-hydroxy benzenecarboximidamide;

(3-{[1-(1-Azepanylcarbonyl)-2-(2-naphthylsulfonyl)hydrazino]metyl}phenyl)(imino)methanaminium chloride;

3-({1-(1-Azepanylcarbonyl)2-[(6-methoxy-2-naphthyl) sulfonyl]hydrazino}methyl)-N'-hydroxybenzenecarboximidamide; and

[3-({1-(1-Azepanylcarbonyl)-2-[(6-methoxy-2-naphthyl) sulfonyl]hydrazino}methyl) phenyl](imino)methanaminium chloride.

4. A method for inhibiting blood coagulation comprising contacting a sample of blood or plasma with a compound of formula I according to claim 1.

5. A process for preparing a compound of formula I according to claim 1, comprising:
converting 3-cyanobenzaldehyde of formula (II)

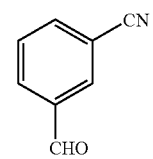

with BOC-carbazate of formula (III)

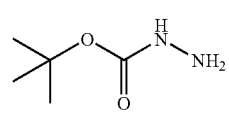

to a compound of formula (IV),

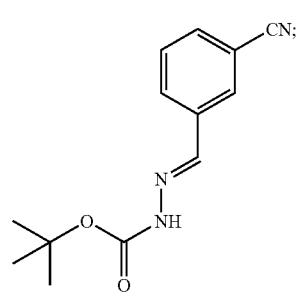

reducing the compound of formula (IV) by catalytic hydrogenation or with NaCNBH₃ to a compound of formula (V),

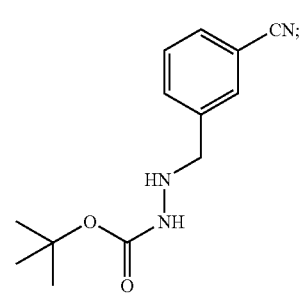

reacting the compound of formula (V) with triphosgene and an amine of formula (VIII),

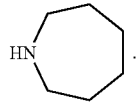 (VIII)

to yield a compound of formula (XI),

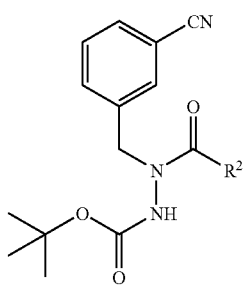 (XI)

wherein R² has the same meaning as in formula (I); removing the protecting BOG group with HG (g) in HOAc at room temperature to obtain a compound of formula (XII),

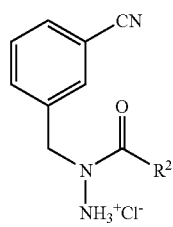 (XII)

wherein R² has the same meaning as in the formula (I); reacting the compound of formula (XII) with aromatic sulfonylchloride to yield a compound of formula (XIII)

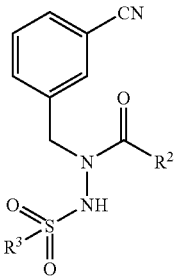 (XIII)

wherein R² and R³ have the same meanings as in formula (I); and converting the compound of formula (XIII) to a compound of formula (I)

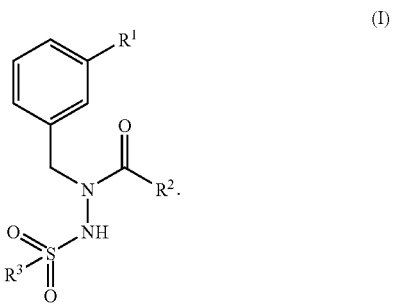 (I)

6. A method for treating blood coagulation disorders in man and other mammals comprising administering a therapeutically effective amount of a compound I as claimed in claim 1, to a subject in need thereof.

7. A pharmaceutical composition comprising a therapeutically effective amount of a compound of formula I as claimed in claim 1 and pharmaceutically acceptable auxiliary substances.

* * * * *